US006655931B2

(12) United States Patent
Nacher

(10) Patent No.: US 6,655,931 B2
(45) Date of Patent: Dec. 2, 2003

(54) PERISTALTIC COMPRESSORS SUITABLE FOR RELAXATION-FREE COMPRESSION OF POLARIZED GAS

(75) Inventor: Pierre-Jean Nacher, Ivry sur Seine (FR)

(73) Assignee: Centre National de la Recherche Scientifique CNRS, Paris (FR)

( * ) Notice: Subject to any disclaimer, the term of this patent is extended or adjusted under 35 U.S.C. 154(b) by 0 days.

(21) Appl. No.: 09/885,653

(22) Filed: Jun. 20, 2001

(65) Prior Publication Data
US 2002/0018728 A1 Feb. 14, 2002

Related U.S. Application Data

(63) Continuation of application No. PCT/FR99/03205, filed on Dec. 20, 1999.

(30) Foreign Application Priority Data

Dec. 23, 1998 (FR) .............................................. 98 16366

(51) Int. Cl.⁷ ................................................ F04B 35/00
(52) U.S. Cl. .................................... 417/375; 417/477.1
(58) Field of Search ....................... 417/53, 375, 477.1; 62/608

(56) References Cited

U.S. PATENT DOCUMENTS

| 5,049,048 A | 9/1991 | Streicher | |
| 5,342,182 A | 8/1994 | Montoya | |
| 5,545,396 A | 8/1996 | Albert | |
| 5,577,891 A | * 11/1996 | Loughnane et al. | 417/53 |
| 8,282,920 | * 9/2001 | Nacher et al. | 62/608 |

FOREIGN PATENT DOCUMENTS

| DE | 37 03 124 A1 | 8/1988 | |
| EP | 0339110 | * 4/1988 | G07F/13/06 |
| EP | 0 869 283 A1 | 10/1998 | |
| FR | 1394 047 A | 7/1965 | |
| FR | 1 431 105 A | 5/1966 | |
| FR | 2 744 932 A1 | 8/1997 | |
| NL | 21 604 C | 10/1929 | |

OTHER PUBLICATIONS

Rosen, M. S. et al., "Polarized 129Xe optical pumping/spin exchange and delivery system for magnetic resonance spectroscopy and imaging studies" Review of Scientific Instruments, 'Online!vol. 70, No. 2, Février 1999 (1999–02), pp. 1546–1552, XP002131321 Retrieved from the Internet: <URL:http://www.hyperfine–research.com/> figure 2.

* cited by examiner

Primary Examiner—Teresa Walberg
Assistant Examiner—L Fastovsky
(74) Attorney, Agent, or Firm—Piper Rudnick LLP

(57) ABSTRACT

A peristaltic compressor suitable for relaxation-free compression of polarized gas including a pumping rotor driven by a motor provided with a plurality of rollers, and at least a tube, wherein the rotor and the tube(s) is(are) placed in a depressurized chamber having a lower pressure than atmospheric pressure, and wherein the motor is formed by at least one tube fed by a pressurized fluid, driving into rotation a peristaltic rotor provided with rollers, coupled with the pumping rotor.

11 Claims, 1 Drawing Sheet

PERISTALTIC COMPRESSORS SUITABLE FOR RELAXATION-FREE COMPRESSION OF POLARIZED GAS

RELATED APPLICATION

This is a continuation of International Application No. PCT/FR99/03205, with an international filing date of Dec. 20, 1999, which is based on French Patent Application No. 98/16366, filed Dec. 23, 1998.

FIELD OF THE INVENTION

This invention relates to the field of peristaltic compressors. This type of compressor uses the principle of peristaltic pumps, wherein a set of rollers presses a flexible tube and upon their rotation around an axis, causes the fluid which is contained in the tube to flow forwards.

BACKGROUND

Peristaltic compressors of the prior art mainly operate under pressure. Under vacuum pressure, the tube in which the fluid flows, tends to be squeezed, preventing the pump from operating. As an example of a peristaltic pump known from the prior art, French Patent 2640698 describes a peristaltic pump including several pinch valves with sleeves pinched by a pressurized fluid. Its body consists of at least two modules placed in series and each including a sleeve. The ends of each sleeve are sealably secured to the edges of the suction and discharge port of each module. The module located on the inlet side of the pump plays the role of a suction valve. The module located on the outlet side of the pump plays the role of a discharge valve.

European Patent 869283 relates to a peristaltic pump including a rotor preferably with two or three rollers which roll against at least one tube containing the liquid to be pumped. Compression of the tube presses the rollers against the circular peripheral surface of a vibrating central stator in the shape of a disc or ring, which guides the rollers and causes them to rotate. The stator is put into vibration by piezoelectric means and vibrates by expansion in its radial plane according to a progressive wave. The chassis of the rotor is without any central shaft.

German Patent 370124 describes a pump with a flexible core comprising:

a) a casing including:

a1) a suction manifold and a compression manifold, a2) a peripheral wall which, at least in a squeezing area located along the long linking part between the suction manifold and the compression manifold, has the shape of a circular section cylinder and a3) a plane front wall and a plane rear wall, b) a flexible tube which runs from the suction manifold to the compression manifold along the peripheral wall into the squeezing area and the periphery of which essentially corresponds to double the distance between the front wall and the rear wall, c) a rotor with its rotation axis coinciding with the axis of the squeezing area of the peripheral wall and with a circular section cylinder shape, and which includes at least two collapsible bodies symmetrically positioned relatively to a point and which rotates in such a way that each collapsible body squeezes the flexible tube from the suction manifold area to the compression manifold area.

A separator device sealably isolates a suction area, i.e., a portion of the inside of the pump wherein vacuum pressure prevails during the pumping, from a compression area in which no vacuum pressure prevails.

The separator device includes a device providing a seal at the rotor and an elastic gasket. The device providing the seal at the rotor, is secured to the rotor and sealably separates the latter from the front wall and the rear wall.

U.S. Pat. No. 5,049,048 describes a tubular pump including a case with a discharge fitting and a suction fitting. A first tube is connected to the discharge and suction fittings and laid out against the inner wall of the case. Compression components may move along the tube in such a way that said tube may be compressed by each of the compression components from the direction of the suction fitting to the direction of the discharge fitting. The pump includes at least a second elastically deformable tube with one of its ends ending in the inner portion of the case whereas its other end ends outside said case.

U.S. Pat. No. 5,261,793 relates to a compressor with which very low pressures may be achieved by selection of a suitable tube (sufficiently small diameter, sufficiently thick wall) in order to prevent its flattening (Col. 5, lines 10–12). This constraint on the selection of the tube is a priori a nuisance for application to the polarized gas: a small section increases the surface/volume ratio and increases relaxation for the polarized gas; a small section reduces the pump flow rate, all things being equal for that matter.

In addition, it is important to be able to select the type of material for the tube according to its compatibility properties with the application to polarized gas, without being restricted to the stiffest tubes. French Patent 1394047 A describes a compressor wherein both evacuation of the pump body and its driving by a peristaltic motor appear. On the other hand, this is not a peristaltic pump, as the fluid is contained not in a tube but in a deformable compartment sealed by rubber membranes. Such a compressor is totally unsuitable for producing a compressor polarized gas.

SUMMARY OF THE INVENTION

This invention relates to a peristaltic compressor suitable for relaxation-free compression of polarized gas including a pumping rotor driven by a motor provided with a plurality of rollers, and at least a tube, wherein the rotor and the tube(s) is(are) placed in a depressurized chamber having a lower pressure than atmospheric pressure, and wherein the motor is formed by at least one tube fed by a pressurized fluid, driving into rotation a peristaltic rotor provided with rollers, coupled with the pumping rotor.

This invention also relates to a system for producing hyperpolarized helium by optical pumping including a peristaltic compressor formed with a magnetic parts exclusively and including a rotor driven by a motor provided with a plurality of rollers, and at least one tube, wherein the rotor and pumping tubes are located in a depressurized chamber inside which has a pressure lower than atmospheric pressure.

BRIEF DESCRIPTION OF THE DRAWING

The drawing is a schematic perspective view of a peristaltic pump in accordance with aspects of the invention.

DETAILED DESCRIPTION

Figure 1:
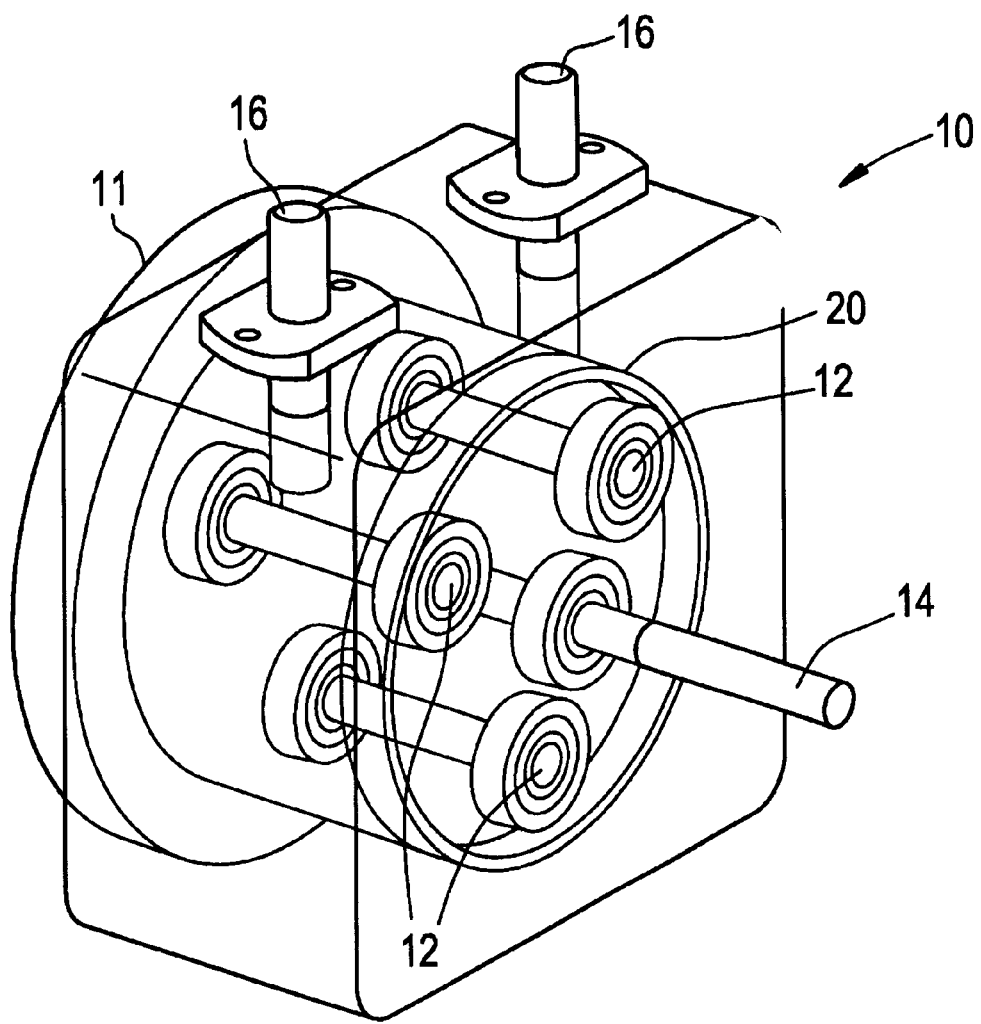

It is an object of the invention to overcome a first drawback of peristaltic pumps of the prior art which result from the presence of metal parts, notably magnetic parts. These magnetic parts prevent them from being used for compressing and pumping polarized gases. To overcome this drawback, the invention exploits the reversibility and driving effect of a peristaltic device so as not to require an external motor for driving the pressing rollers. With this in particular, it is possible to have an a magnetic device without an electric power supply. This is important for compressing polarized gas without causing any relaxation, in particular, within a NMR imaging apparatus or in an area with a strong magnetic field or the like.

The invention also avoids the drawback of the pumps from the state of the art, whereby their operation does not allow significant vacuum pressure levels to be attained because of the squeezing of the tubes. When the tubes contain a fluid at a lower pressure than atmospheric pressure, they retain the deformation produced by the rollers of the rotor and they do not recover their initial volume. To overcome this drawback, the invention in its most general form as shown in the drawing is a peristaltic compressor 10 suitable for the relaxation-free compression of polarized gas including a rotor 14 driven by a motor 20 provided with a plurality of rollers 12, and at least a tube 16 wherein the rotor and the pumping tubes are placed in a depressurized chamber 11 inside which prevails a lower pressure than the atmospheric pressure, characterized in that the motor is formed by at least one tube fed by a pressurized fluid, driving into rotation a peristaltic rotor provided with rollers, coupled with the pumping rotor.

The invention according to an advantageous alternative embodiment, relates to a peristaltic pump including a rotor driven by a motor provided with a plurality of rollers, and at least a tube, characterized in that the motor is formed by at least a tube supplied with a pressurized fluid, driving into rotation a peristaltic rotor provided with rollers coupled with the pumping rotor. Advantageously, the driving rotor and the pumping rotor form a single part.

According to a preferred embodiment, the device includes an alternation of tubes for pumping and compressing, and tubes for driving the motor. Also according to a preferred embodiment, the invention relates to a peristaltic compressor suitable for the relaxation-free compression of polarized gas, including a magnetic parts exclusively.

According to an advantageous alternative embodiment, the rotor comprises two or three freely rotatable rollers. Preferably, the driving and pumping tubes are shifted angularly.

According to a particular alternative embodiment, the device comprises a central tube for pumping, and two side tubes for driving the rotor, positioned on both sides of the central tube. Preferably, the driving tube(s) receive(s) a fluid under a pressure between about 1 and about 5 bars.

According to a preferred alternative embodiment, the rotor and the pumping tubes are placed in a depressurized chamber inside which prevails a lower pressure than atmospheric pressure. Advantageously, the depressurized chamber is connected to a vacuum pressure source.

The present invention in particular solves the problem of efficiently compressing a strongly polarized gas (or gaseous mixture) by a simple device and without significant polarization loss. This problem is encountered upon preparing polarized helium-3 by optical pumping at 1,083 nm, a method which is only efficient at gas pressure, less than atmospheric pressure, for all applications where a larger pressure is required. Thus, according to the method used, the polarized gas has a pressure on the order of one millibar, or else of a few tens to hundreds of millibars, whereas applications such as in vivo imaging of air spaces, require gas at one bar or more. This problem may also be encountered for xenon polarized by optical pumping, or more generally for any gas or gaseous mixture for which transfer and/or build-up in a given volume is desirably forced, without significantly affecting the non-equilibrium nuclear polarization (hyperpolarization) of this gas.

Techniques used hitherto for fulfilling this function are based on cryogenic or mechanical devices. Cryogenic devices, which use a cycle with a change of phase for the polarized gas (helium liquefaction, xenon liquefaction or solidification), cannot be applied to all gaseous mixtures and they are not simple to implement in all the environments. The usual mechanical compressing devices (piston, membrane, vane pumps and the like) have the drawback of only providing a limited compression ratio (and, therefore, they virtually require several stages) and of being very delicate to adapt to the strict a magnetism conditions required by the relaxation-free compression of polarized gas.

In addition, there is a further problem for mechanically driving a compressor, which cannot be provided by an electrical motor (which generates magnetic fields causing a rapid loss of gas polarization) positioned near the compressor.

A peristaltic pump provides a certain number of advantages for polarized gases as compared with cryogenic or mechanical devices. A priori, it allows a given volume flow rate without any theoretical limit on the compression ratio, and it may easily be produced with a magnetic, even non-metal materials. It may, therefore, operate in any (including a strong magnetic field) environment and without inducing any notable nuclear relaxation. On the other hand, it is a priori unsuitable for providing flow compression of a fluid at a notably lower pressure than atmospheric pressure (this pressure flattens flexible tubes, and virtually prevents any fluid flow at an absolute pressure less than about 0.7 or about 0.8 bars). In addition, the problem of its mechanical drive is the same as the one discussed earlier for other types of mechanical compressors.

Both improvements presented in the general principle of the invention and detailed hereafter, provide a final solution to the latter problems of a peristaltic pump, which are in particular encountered for compressing or handling of hyperpolarized gas in very restricting environments.

A very simple compressor device suitable for the relaxation-free compression of polarized gas (i.e., without inducing any significant polarization loss) will be described herein. This device is particularly suitable for the compression of helium produced according to methods forming the subject of French Patent 2744932, dealing with a method allowing high pressure helium gas to be polarized by optical pumping. It may also be used for the relaxation-free compression of polarized gas produced at a lower pressure by conventional techniques, or even for transferring a polarized gas from one container to another.

An important application of the device relates to the compression of helium gas polarized by optical pumping. In the text of the already mentioned patent, reference will be found to the traditional polarization technique by means of optical pumping applied on the atomic transition of a wavelength close to 1,083 nm, in the presence of a low magnetic field (generally on the order of one milliTesla): under these conditions, the optical pumping is only efficient when the gas pressure in on the order of one millibar (1 mbar=100 Pa).

This same text describes how efficient optical pumping may be conducted by the wise use of a sufficiently strong magnetic field, in a large range of gas pressures, which, however, remain less than atmospheric pressure (commonly 10–100 mbars). For certain applications, this gas (pure, or mixed with another gas) is brought up to atmospheric pressure before it may be used; e.g. for in vivo magnetic resonance imaging, the gas must be able to be inhaled by a subject. For storage or transport, the gas is advantageously brought up to a pressure of several bars in suitable containers. Finally it is extracted from them for the desired final use.

By optical pumping of helium at 1,083 nm, the nuclei of the gas may be polarized at a rate depending on many parameters, the available light intensity inclusive, and this rate may vary from about $10^{17}$ to about $10^{19}$ atoms per second. In a steady state mode, this corresponds to gas volume flow rates inversely proportional to pressure P, examples of which are given in the table below:

| Polarization rate (atoms/s) | Typical laser power (at 1,083 nm) | Flow rate at P = 1 mbar low magnetic field | Flow rate at P = 30 mbars strong magnetic field |
| --- | --- | --- | --- |
| $10^{17}$ | 50 mW | 0.22 1/min | 7 cm³/min |
| $10^{19}$ | 5 W | 22 1/min | 0.7 1/min |

These order of magnitude clearly show the flow rate characteristics which are required for a compressor device, depending on the laser source used and on the pressure at which optical pumping in conducted. The volume flow rate of a peristaltic pump is the product of the internal section of the tube used, by the linear velocity of the pressing rollers. For the prototype device which we have produced, this section is 0.4 cm², and rotation at 1,200 rpm causes a flow rate (per tube) on the order of 14 1/min. Such features are quite suitable for the typical rates required in various situations, several tubes in parallel (or a tube with a larger section) provide greater flow rate at a given speed of rotation.

There is no basic limit on the compression ratio attained by a peristaltic pump. Practically, the maximum attained pressure is limited by the overpressure resistance of the tube used (about 2 to about 3 bars, frequently). The minimum pressure at which a pump operates, is conventionally limited by the capability of the tube of resuming its shape (circular section) after the passing of a pressing roller. Its elasticity is generally insufficient in the presence of an external overpressure which keeps it flattened.

According to one of the features of the invention, i.e., operation in a vacuum chamber, the internal pressure of the tube is always higher than that of the chamber in which it is immersed, and the rated flow rate remains the same until substantially zero pressure. Accordingly, a simple peristaltic pump stage operating in a vacuum chamber is suitable for compressing gas from a pressure suitable for optical pumping of helium up to a pressure which may attain about 2 bars, for example. If higher pressures need to be attained, a second compression stage may be used; it will even be possible to use for this purpose, a peristaltic pump operating in a pressurized chamber so as to be no longer limited by the overpressure resistance of the tube used.

For all applications in which polarized gas is handled, it is appropriate to use devices which do not induce magnetic field inhomogeneities at the gas level.

Such inhomogeneities are indeed likely to induce a rapid nuclear relaxation towards a quasi-zero polarization value. These inhomogeneities may occur on a large scale and affect the volume of the gas. To avoid the latter, it is appropriate not to use materials having significant magnetic susceptibility, and this all the more the nearer they are to the polarized gas. Of course, ferromagnetic materials should be banned, but the use of a large number of alloys commonly used for their mechanical properties (Stainless steels, brass, bronze and the like) should also be avoided. Use of electric motors generating very inhomogeneous magnetic fields, is generally impossible at distances less than one or a few meters. Finally, it may be advantageous, for example, in the presence of strong electro-magnetic field s such as those encountered with MRI apparatuses, to ban any conducting metal parts. We shall see in the produced example of the device that we were able to comply with these restrictions without any inconvenience.

These magnet field inhomogeneities may also be induced at a microscopic scale by the surface characteristics of the materials directly in contact with the polarized gas. Further, no contamination of the polarized gas, whether chemical or biological, should result from contact of the gas with these materials. This is particularly important for application in which the gas is subsequently inhaled, but the purity of the gas is also essential during the polarization process by optical pumping (no impurity should be able to diffuse from the compressor device into the optical pumping volume), and it may pay a role in the nuclear relaxation of the gas during its subsequent transport or storage. As for these various points, it is appropriate to take all precautions upon selecting the materials which come into direct contact with the gas, and to use configurations able to prevent any contamination of the gas in the optical pumping volume. These constraints could also be complied with for the produced device.

One of the points discussed above—the absence of any contamination of the gas upstream from the compressor by impurities which the latter inevitably introduces—imposes the design of a monotonous flow device, without any discharge.

In a peristaltic pump, rotation of the rollers drives the fluid in the tube in the direction of rotation in a monotonous and regular way. However, when a roller comes into contact with the tube and compresses it, it causes a reduction of the accessible volume to the fluid at the inlet of the pump, which tends to reverse the flow of the fluid. The competition between these two effects may possibly cause a net backflow of the fluid for certain positions of the rollers, according to the ratio of the respective diameters of the rollers and of the roller path where the tube is pressed (the net consequences of these effects also specifically depends on how the tube is gradually squeezed).

A peristaltic device, if it is always used in practice for outputting or compressing a fluid, may also be used as a motor: when a pressure differential is applied to the fluid contained in the tube, a driving torque is applied to the rollers. This torque may directly be inferred by deriving the effect of the rotation on the flow rate. In most industrial realizations of peristaltic pumps, geometrical characteristics are such that a backflow of the fluid occurs several times per revolution; in this case, the driving torque changes sign during the rotation and continuous rotation is not possible. On the other hand, when the geometrical characteristics are adequate, the driving torque has a constant sign and continuous rotation becomes possible, subject to the condition that power dissipation by friction does not exceed the driving power. In the case of the produced device, it was possible to obtain a large operating range for the motor.

The peristaltic pump suitable for compressing polarized gas includes one or more tubes placed inside an essentially cylindrical volume, traditionally serving as a supporting surface for the tubes, but built such as to be airtight with regards to the surround air. According to the retained configuration, sealed passages enable inflow and outflow of the fluid flowing in the tubes. A rotor including at least two rollers, for example, three in the described example, which may rotate freely on their axis, is positioned to suitably compress the tube(s).

For an entirely pneumatic operation, three tubes are used: two are submitted to an adjustable pressure of pressurized air or water and the resulting torque is sufficient for driving the rotor. The third tube may then be used for causing a fluid to flow or to be compressed, polarized gas, for example. For operating as a simple pump, a rotating axis sealably crossing the wall of the pump is used for mechanically driving the rotor.

In both cases, the pressure of the internal volume of the device may be adjusted and, in particular, be made sufficiently low to allow pumping of the fluid at an arbitrarily low pressure, according to one of the alternative embodiments of the invention. This device operates in a satisfactory way and all the materials and parts which it includes, do not cause any magnetic relaxation in their immediate vicinity. Depending on the result, specific devices are developed for particular uses. According to the production rate provided by the laser source, and according to the contemplated type of use, it might in particular be more advantageous to make use of a peristaltic motor or to use a standard motor.

For most applications, the hyperpolarized gas (helium or xenon) should be produced or brought up to a pressure on the order of atmospheric pressure. Presently, two kinds of methods are used for producing a polarized gas with a high polarization:

Polarization of helium-3 or xenon by spin exchange with a gas of alkaline atoms orientated by optical pumping (for example, a rubidium vapor). In the case of alkaline atoms, the pumping operates on the ground state of the atoms. As no discharge is required in the gas, the pumping may basically operate at any pressure. Unfortunately, this method is intrinsically very slow, as exchange collisions which provide transfer of polarization from the alkaline atom to the noble gas are not very efficient and are a limiting factor which cannot be ignored. Hence, 4 to 8 hours, are, for example, required for polarizing 100 cc of helium at a pressure of 3.5 to 8 bars with a polarization from 5 to 20%. In the case of xenon, it is much more favorable to work with low xenon pressure and its build-up is achieved by means of a cryogenic technique.

Polarization by optical pumping at 1,083 nm, with a discharge in a low pressure gas, is followed by a compression of the polarized gas. If the optical pumping is a very efficient step, today, compression requires complex techniques which have only been developed in a few laboratories. A method consists in using a mechanical compressor with mobile pistons, specially designed for retaining the polarization and the purity of the gas.

A second method, developed by the Applicant and described in French Patent 2744932 uses a cryogenic technique for compression. A prototype of a simpler device, based on a commercial model of a membrane pump drastically changed to reduce the relaxation potential of the materials usually used, has also been developed at NIST (Washington, USA) and is now used for imaging tests with hyperpolarized helium. Finally, there is the technical difficulty in mechanical compression that may be strongly reduced by conducting optical pumping at a higher pressure which reduces the required compression ratio and volume flow rate for the compressor device.

Helium-3 may also be substantially polarized in a spontaneous way, but in a very strong magnetic field and at very low temperature. Various systems may be used (fusion of a solid polarized at thermal equilibrium, extreme cooling of very dilute isotope mixtures, overpolarization by pseudo-distillation of demixed liquid mixtures and the like), but they require very sophisticated techniques and have only been used very recently for producing polarized gas (at Grenoble) with a very modest polarization (on the order of one percent).

A peristaltic compressor device which integrates the introduced innovations enables hyperpolarized gas to be compressed and is compatible with the use of various optical pumping techniques. It provides a number of advantages over other compression devices:

As compared with other mechanical compression methods, peristaltic compression has the basis advantage of not having any limit as to the compression ratio which may be obtained (in only one single step), and of not requiring mobile parts (flaps, valves, gates or the like) in contact with the polarized gas, for which experience shows that it is very delicate to produce them without introducing significant relaxation. The introduced innovations enable such devices to pump a fluid at an arbitrarily low pressure and, if necessary, to be rid of the mechanical driving problems of the pump. So it is now known how to make a very simple device, made out of common materials and without the disadvantage of relaxation, which enables polarized gas to be compressed and/or to flow. With the simplicity of the manufacturing and compactness of such devices, they may be produced at a very modest price.

As compared with cryogenic methods, the device is generally preferred because of its simplicity, portability and ease of use.

A hyperpolarized helium production system using such a device is, therefore, sufficiently simple to be able to operate outside a laboratory and, for example, to be ported or implemented on the site of use. In addition to its essential use for producing gas by optical pumping, this device may also be integrated into systems monitoring flow of polarized gas between containers, or even for controlled administration of polarized gas in patients or subjects under MRI examination.

What is claimed is:

1. A peristaltic compressor suitable for relaxation-free compression of polarized gas comprising a pumping rotor driven by a motor provided with a plurality of rollers, and at least a tube, wherein the rotor and the tube(s) is(are) placed in a depressurized chamber having a lower pressure than atmospheric pressure, and wherein the motor is formed by at least one tube fed by a pressurized fluid, driving into rotation a peristaltic rotor provided with rollers, coupled with the pumping rotor.

2. The peristaltic compressor according to claim 1, including alternating 1) tubes for pumping and compressing and 2) tubes for driving the motor.

3. The peristaltic compressor according to claim 2, comprising a magnetic parts exclusively.

4. The peristaltic compressor according to claim 1, wherein the rotor comprises two or three freely rotatable rollers.

5. The peristaltic compressor according to claim 2, wherein the pumping and driving tubes are shifted angularly.

6. The peristaltic compressor according to claim 1, wherein there is a central tube for pumping, and two side tubes for driving the rotor, positioned on both sides of the central tube.

7. The peristaltic compressor according to claim 2, wherein the driving tube receives a fluid under a pressure of about 1 to about 5 bars.

8. The peristaltic compressor according to claim 1, wherein the driving rotor and the pumping rotor form a single part.

9. The peristaltic compressor according to claim 8, wherein the depressurized chamber is connected to a vacuum pressure source.

10. A system for producing hyperpolarized helium by optical pumping comprising a peristaltic compressor formed with amagnetic parts exclusively and including a rotor driven by a motor provided with a plurality of rollers, and at least one tube, wherein the rotor and pumping tubes are positioned in a depressurized chamber inside which has a pressure lower than atmospheric pressure.

11. The system for producing hyperpolarized helium by optical pumping according to claim 10, further comprising means for controlled administration of polarized gas in patients or subjects under MRI examination.

* * * * *

UNITED STATES PATENT AND TRADEMARK OFFICE
CERTIFICATE OF CORRECTION

PATENT NO. : 6,655,931 B2
APPLICATION NO. : 09/885653
DATED : December 2, 2003
INVENTOR(S) : Nacher It is certified that error appears in the above-identified patent and that said Letters Patent is hereby corrected as shown below:

In Column 2
At line 50, please change "a magnetic" to --non-magnetic--.

In Column 3
At line 3, please change "a magnetic" to --non-magnetic--; at line 39, please change "a magnetic" to --non-magnetic--.

In Column 4
At line 15, please change "a magnetism" to --non-magnetism--; and at line 27, please change "a magnetic" to --non-magnetic--.

In Column 8
Line 2 of Claim 3, please change "a magnetic" to --non-magnetic--.

In Column 10
Claim 10, Line 1, please change "amagnetic" to --non-magnetic--.

Signed and Sealed this

Thirtieth Day of March, 2010

David J. Kappos
*Director of the United States Patent and Trademark Office*